United States Patent [19]
Anton et al.

[11] Patent Number: 5,541,094
[45] Date of Patent: Jul. 30, 1996

[54] GLYOXYLIC ACID/AMINOMETHYLPHOSPHONIC ACID MIXTURES PREPARED USING A MICROBIAL TRANSFORMANT

[75] Inventors: David L. Anton; Robert DiCosimo, both of Wilmington, Del.

[73] Assignee: E. I. du Pont de Nemours and Company, Wilmington, Del.

[21] Appl. No.: 253,823

[22] Filed: Jun. 3, 1994

Related U.S. Application Data

[63] Continuation of Ser. No. 26,615, Mar. 3, 1993, abandoned, which is a continuation of Ser. No. 951,497, Sep. 25, 1992, abandoned.

[51] Int. Cl.$^6$ .............................. C12P 7/40; C12P 13/00; C12N 9/04
[52] U.S. Cl. .................. 435/136; 435/190; 435/192; 435/172.1
[58] Field of Search ................................ 435/136, 190, 435/192, 172.1

[56] References Cited

U.S. PATENT DOCUMENTS

| | | | |
|---|---|---|---|
| 3,281,460 | 10/1925 | Gandon .................................. | 260/530 |
| 4,094,928 | 6/1978 | Gaertner et al. ........................ | 206/944 |
| 4,146,731 | 3/1979 | Ogahara et al. ......................... | 562/531 |
| 4,233,452 | 11/1980 | Williams et al. ........................ | 549/79 |
| 4,235,684 | 11/1980 | Harada et al. ............................ | 204/79 |
| 4,455,371 | 6/1984 | Richardson et al. ..................... | 435/25 |
| 4,670,191 | 6/1987 | Kleiner et al. ..................... | 260/502.5 F |
| 4,871,669 | 10/1989 | Murray et al. .......................... | 260/530 |
| 4,935,349 | 6/1990 | McKnight et al. .................... | 435/69.5 |
| 5,000,000 | 3/1991 | Ingram .................................... | 435/161 |
| 5,135,860 | 8/1992 | Anton et al. ............................ | 435/136 |
| 5,180,846 | 1/1993 | Anton et al. .............................. | 562/17 |
| 5,219,745 | 6/1993 | Anton et al. ............................ | 435/136 |
| 5,221,621 | 6/1993 | Anton et al. ............................ | 435/136 |

OTHER PUBLICATIONS

Macheroux et al., "Expression of Spinach Glycolate Oxidase in *Saccharrmyces cerevisiae:* Purification and Characterization", *Biochemistry,* vol. 30, pp. 4612–4614. 1991.
Creuger et al, In: Biotechnology: A Textbook of Industrial Microbiology: Publisher: Sinauer Associates, Inc.; pp. 290–291 1989.
Tolbert, N. E. et al, *J. Biol. Chem.,* 181, 905–914 (1949).
Richardson et al, *J. Biol. Chem.,* 236, 1280–1284 (1961).
Clagett et al, *J. Biol. Chem.,* 178, 977–987 (1949).
Zelitch et al, *J. Biol. Chem.,* 201, 707–718 (1953).
Robinson et al, *J. Biol. Chem.,* 237, 2001–2009 (1962).
Frigerio et al, *J. Biol. Chem.,* 231, 135–157 (1958).
Volokita, M. et al, *J. Biol. Chem.,* 262(33), 15825–15828 (1987).
Zelitch, *Methods of Enzymology,* 1, Academic Press, New York, 528–532 (1955).
Nishimura, M. et al, *Arch. Biochem. Biophys.,* 222, 397–401 (1983).
Asker et al, *Biochem. Biophys. Acta.,* 761, 103–108 (1983).
Emes et al, *Int. J. Biochem.,* 16, 1373–1378 (1984).
Cederlund et al, *Eur. J. Biochem,* 173, 523–530 (1988).
Lindquist et al, *J. Biol. Chem.,* 264, 3624–3628 (1989).

*Primary Examiner*—John W. Rollins
*Assistant Examiner*—Francisco C. Prats

[57] ABSTRACT

An improved enzymatic process for reacting glycolic acid and oxygen in an aqueous solution in the presence of aminomethylphosphonic acid wherein the improvement comprises using a microbial cell catalyst that expresses glycolate oxidase (e.g., *Pichia pastoris, Hansenula polymorpha, Aspergillus nidulans,* or *Escherichia coli*) and endogenous catalase; soluble catalase may also be included. The resulting mixtures are useful intermediates in the production of N-(phosphonomethyl)glycine.

5 Claims, No Drawings

GLYOXYLIC ACID/AMINOMETHYLPHOSPHONIC ACID MIXTURES PREPARED USING A MICROBIAL TRANSFORMANT

This is a continuation of application Ser. No. 08/026,615, filed Mar. 3, 1993, now abandoned, which is a continuation of application Ser. No. 07/951,497, filed on Sep. 25, 1992, abandoned.

BACKGROUND OF THE INVENTION

1. Field of the Invention

This invention relates to a process for the production of mixtures of glyoxylic acid and aminomethylphosphonic acid (AMPA), where glycolic acid and oxygen are reacted in an aqueous solution in the presence of AMPA and catalysts consisting of a genetically-engineered microbial transformant which expresses the enzyme glycolate oxidase from spinach ((S)-2-hydroxy-acid oxidase, EC 1.1.3.15), and catalase (EC 1.11.1.6). The glyoxylic acid/aminomethylphosphonic acid mixtures prepared in this manner are useful intermediates in the production of N-(phosphonomethyl)glycine, a broad-spectrum, post-emergent herbicide.

2. Description of the Related Art

Glycolate oxidase, an enzyme commonly found in leafy green plants and mammalian cells, catalyzes the oxidation of glycolic acid to glyoxylic acid, with the concomitant production of hydrogen peroxide:

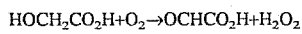

N. E. Tolbert et al., *J. Biol. Chem.*, Vol. 181, 905–914 (1949) first reported an enzyme, extracted from tobacco leaves, which catalyzed the oxidation of glycolic acid to formic acid and $CO_2$ via the intermediate formation of glyoxylic acid. The addition of certain compounds, such as ethylenediamine, limited the further oxidation of the intermediate glyoxylic acid. The oxidations were carried out at a pH of about 8, typically using glycolic acid concentrations of about 3–40 mM (millimolar). The optimum pH for the glycolate oxidation was reported to be 8.9. Oxalic acid (100 mM) was reported to inhibit the catalytic action of the glycolate oxidase. Similarly, K. E. Richardson and N. E. Tolbert, *J. Biol. Chem.*, Vol. 236, 1280–1284 (1961) showed that buffers containing tris(hydroxymethyl)aminomethane (TRIS) inhibited the formation of oxalic acid in the glycolate oxidase catalyzed oxidation of glycolic acid. C. O. Clagett, N. E. Tolbert and R. H. Burris, *J. Biol. Chem.*, Vol. 178, 977–987 (1949) reported that the optimum pH for the glycolate oxidase catalyzed oxidation of glycolic acid with oxygen was about 7.8–8.6, and the optimum temperature was 35°–40° C.

I. Zelitch and S. Ochoa, *J. Biol. Chem.*, Vol. 201, 707–718 (1953), and J. C. Robinson et al., *J. Biol. Chem.*, Vol. 237, 2001–2009 (1962), reported that the formation of formic acid and $CO_2$ in the spinach glycolate oxidase-catalyzed oxidation of glycolic acid resulted from the nonenzymatic reaction of $H_2O_2$ with glyoxylic acid. They observed that addition of catalase, an enzyme that catalyzes the decomposition of $H_2O_2$, greatly improved the yields of glyoxylic acid by suppressing the formation of formic acid and $CO_2$. The addition of FMN (flavin mononucleotide) was also found to greatly increase the stability of the glycolate oxidase.

N. A. Frigerio and H. A. Harbury, *J. Biol. Chem.*, Vol. 231, 135–157 (1958) have reported on the preparation and properties of glycolic acid oxidase isolated from spinach. The purified enzyme was found to be very unstable in solution; this instability was ascribed to the relatively weak binding of flavin mononucleotide (FMN) to the enzyme active site, and to the dissociation of enzymatically active tetramers and/or octamers of the enzyme to enzymatically-inactive monomers and dimers, which irreversibly aggregate and precipitate. The addition of FMN (flavin mononucleotide) to solutions of the enzyme greatly increased its stability, and high protein concentrations or high ionic strength maintained the enzyme as octamers or tetramers.

There are numerous other references to the oxidation of glycolic acid catalyzed by glycolate oxidase. The isolation of the enzyme (and an assay method) are described in the following references: I. Zelitch, *Methods of Enzymology*, Vol. 1, Academic Press, New York, 1955, p. 528–532 (from spinach and tobacco leaves), M. Nishimura et al., *Arch. Biochem. Biophys.*, Vol. 222, 397–402 (1983) (from pumpkin cotyledons), H. Asker and D. Davies, *Biochem. Biophys. Acta*, Vol. 761, 103–108 (1983) (from rat liver), and M. J. Emes and K. H. Erismann, *Int. J. Biochem.*, Vol. 16, 1373–1378 (1984) (from *Lemna Minor L*). The structure of the enzyme has also been reported: E. Cederlund et al., *Eur. J. Biochem.*, Vol. 173, 523–530 (1988), and Y. Lindquist and C. Branden, *J. Biol. Chem.*, Vol. 264, 3624–3628, (1989).

SUMMARY OF THE INVENTION

This invention relates to the preparation of mixtures of glyoxylic acid (or a salt thereof) and aminomethylphosphonic acid (AMPA) (or a salt thereof), by oxidizing glycolic acid with oxygen in aqueous solution and in the presence of AMPA and two catalysts: a genetically-engineered microbial transformant which expresses the enzyme glycolate oxidase from spinach ((S)-2-hydroxy-acid oxidase, EC 1.1.3.15), and catalase (EC 1.11.1.6). Such mixtures of glyoxylic acid and AMPA are useful for the preparation of N-(phosphonomethyl)glycine, a post-emergent herbicide.

DESCRIPTION OF THE PREFERRED EMBODIMENTS

A related patent, U.S. Pat. No. 5,135,860 (Aug. 4, 1992), "Process for Preparing Glyoxylic Acid/Aminomethylphosphonic Acid Mixtures", describes a process for the enzymatic conversion of glycolic acid to glyoxylic acid in the presence of oxygen, aminomethylphosphonic acid (AMPA), and the soluble enzymes glycolate oxidase and catalase. It was unexpected that the addition of AMPA to enzymatic oxidations of glycolic acid within the pH range of 7 to 9 would result in the high yields of glyoxylic acid obtained, since an unprotonated amine was believed to be necessary to form an oxidation-resistant N-substituted hemiaminal and/or imine complex with glyoxylate. The pKa of the protonated amine of AMPA is reported to be 10.8 (*Lange's Handbook of Chemistry*, J. A. Dean, ed., McGraw-Hill, New York, 1979, 12th edition), therefore AMPA would be present in the reaction mixture predominantly as the protonated ammonium ion and not be expected to form such protective complexes with glyoxylate. The present invention provides an improvement to the above process in the form of a whole microbial cell as a catalyst for this process.

The previously reported use of soluble enzymes as catalysts for the production of glyoxylic acid/aminomethylphosphonic acid mixtures poses several problems: catalyst recovery for reuse is not easily performed, enzyme activity is not as stable as with immobilized enzyme or whole cell catalyst systems, and soluble glycolate oxidase is not stable to the sparging of the reaction mixture with oxygen (required to increase the rate of oxygen dissolution and, thus, reaction rate). A second related patent application, U.S. Ser. No. 08/085,488, filed Jul. 1, 1993, "Glycolate Oxidase Production", described the construction of several transformants of *Aspergillus nidulans* using genetic engineering techniques commonly known to those skilled in the art, which express the glycolate oxidase from spinach as well as an endogenous catalase. The pertinent portions of this patent application as set forth following Example 17. Several advantages for the use of these whole-cell catalysts over the use of soluble enzymes for the production of glyoxylic acid/aminomethylphosphonic acid mixtures in the present invention are:

(1) the whole-cell catalysts are easily recovered from the reaction mixture at the conclusion of the reaction for reuse, whereas the soluble enzyme is only recovered with great difficulty and loss of activity;

(2) they are more stable than the soluble enzyme, both for the number of catalyst turnovers obtained versus the soluble enzyme, as well as for recovered enzyme activity at the conclusion of a reaction; and (3) most importantly, they are stable to reaction conditions where oxygen or an oxygen-containing gas is sparged into the reaction mixture to increase the rate of oxygen dissolution and reaction rate, where under similar reaction conditions the soluble glycolate oxidase is rapidly denatured.

The *Aspergillus nidulans* transformants were prepared by first cloning the spinach gene which codes for glycolate oxidase, then introducing this gene into a strain of *Aspergillus nidulans* which already produced an endogenous catalase. The resulting transformants were cultured in either minimal media or SYG rich media in shaker flasks or fermenters, and additionally, different agents such as oleic acid (OL), hydroxyacetic acid (HA), or corn steep liquor (CSL) were added to the media to increase levels of expression of glycolate oxidase and/or catalase. The different transformants were then screened by assaying the whole cells (untreated) for catalase and glycolate oxidase activity, and by running reactions with the cells as catalysts for the oxidation of glycolic acid to glyoxylic acid.

When used as catalyst for the oxidation of glycolic acid to glyoxylic acid, *Aspergillus nidulans* cells were not pretreated or permeabilized to increase accessibility of the reaction mixture to the enzymes in the interior of the cells; some permeabilization of the cells may take place, possibly from exposure to the reaction mixture or any of its components, or by freezing and thawing, which was used to store the whole cell catalysts until needed.

The use of *Aspergillus nidulans* transformants as a whole cell catalyst for the production of glyoxylic acid has been previously demonstrated (U.S. Ser. No. 08/085,488, filed Jul. 1, 1993, "Oxidation of Glycolic Acid to Glyoxylic Acid using a Microbial Cell Transformant as Catalyst"), where employing an amine buffer (e.g., ethylenediamine or TRIS) capable of forming a chemical adduct with glyoxylic acid resulted in yields of glyoxylic acid as high as 98%; in that case, the concentration of endogenous catalase within the cell was sufficient to limit the oxidation of glyoxylate to formate by byproduct hydrogen peroxide. In the present case, where AMPA is less effective at protecting glyoxylate from oxidation by hydrogen peroxide, the concentration of endogenous *A. nidulans* catalase within the cells was insufficient to produce the desired high yields of glyoxylate. It has been discovered that adding additional soluble catalase (e.g., from *A. niger* or *S. cerevisiae*) to the AMPA-containing reaction mixture which uses these whole cells as a source of glycolate oxidase activity can result in yields of glyoxylate similar to those achieved when using soluble or immobilized enzymes.

When using an *A. nidulans* transformant as catalyst for the oxidation of glycolate/AMPA mixtures, both glyoxylate and hydrogen peroxide are produced within the cells containing the glycolate oxidase, and in the absence of added soluble catalase, glyoxylate is rapidly oxidized to formate (87% formate, 1.6% glyoxylate). It was unanticipated that high yields of glyoxylate could be obtained by simply adding soluble catalase to the reaction, since (1) the relative concentration of glyoxylate and hydrogen peroxide produced throughout the course of the reaction was greater within the cells than in the surrounding aqueous solution, (2) the concentration of endogenous catalase within *A. nidulans* cells was typically 2% to 15% of the concentration of soluble catalase usually added to a reaction mixture, and (3) the hydrogen peroxide would have to diffuse from inside the cell into the surrounding aqueous solution in order to be decomposed to water and oxygen by the soluble catalase. However, yields of glyoxylate as high as 94% have been obtained by simply adding soluble catalase to the reaction mixture at the same concentrations as have been previously employed when using only soluble catalase and soluble glycolate oxidase as catalysts (U.S. Pat. No. 5,135,860).

A second microbial cell catalyst which has been utilized in the present invention is a transformant of *Hansenula polymorpha* (a methylotrophic yeast) which expresses the glycolate oxidase enzyme from spinach, as well as an endogenous catalase. Several transformants of *H. polymorpha* having sufficient glycolate oxidase activity have been prepared by inserting the DNA for glycolate oxidase into an expression vector under the control of the formate dehydrogenase (FMD) promoter. *H. Polymorpha* was transformed with this vector and a strain producing high levels of glycolate oxidase was selected and designated *H. polymorpha* GO1. *H. polymorpha* GO1 was deposited with the Northern Regional Research Laboratories on Mar. 30, 1993 under the terms of the Budapest Treaty and designated accession number NRRL Y-21065.

*H. polymorpha* cell catalysts were typically prepared by first growing an inoculum of an *H. polymorpha* transformant in 500 ml of YPD (Difco), pH 4.4. This culture was then inoculated into a fermenter containing 10 L of Yeast Nitrogen Base (YNB, Difco) w/o amino acids (14 g), ammonium sulfate (50 g) and methanol (100 g), at pH 5.0. The fermenter was operated for 42.5 h at 37° C., an agitation rate of 400 rpm, constant pH of 5.0, 40% dissolved oxygen (controlled), and 14 psig of air. At the conclusion of the fermentation, 1.0 Kg of glycerol was added and the cells harvested by centrifugation, frozen in liquid nitrogen, and stored at −80° C.

A third microbial cell catalyst which has been utilized in the present invention is a transformant of *Pichia pastoris* (a methylotrophic yeast) which expresses the glycolate oxidase enzyme from spinach, as well as an endogenous catalase. Several transformants of *P. pastoris* having sufficient glycolate oxidase activity have been prepared by inserting a DNA fragment containing the spinach glycolate oxidase gene into a *P. pastoris* expression vector (pHIL-D4) such as to be under control of the methanol inducible alcohol oxidase I promoter, generating the plasmid pMP1. *P. pastoris* strain GTS115 (NRRL Y-15851) was transformed by plasmid pMP1 and a selection was done such as to allow integration of the linearized plasmid pMP1 into the chromosomal alcohol oxidase I locus and replacement of alcohol oxidase gene with glycolate oxidase gene. A pool of such transformants were next selected for maximal number of integrated copies of the expression cassette. A high copy number transformant designated *P. pastoris* strain GS115-MSP10 was isolated and deposited in the NRRL, Peoria, Ill., Northern Regional Research Laboratories on Sep. 24, 1992, under the terms of the Budapest Treaty and is designated by the accession number NRRL Y-21001.

*P. pastoris* cells were typically prepared by growing an inoculum in 100 ml of YNB containing 1% glycerol. After 48 hours growth at 30° C., the cells were transferred into a fermenter containing 10 L of media composed of yeast nitrogen base (YNB) w/o amino acids (134 g), glycerol (100 g), and biotin (20 mg). The fermentation was operated at pH 5.0 (controlled with $NH_4OH$), 30° C., agitation rate of 200 rpm, aeration of 5 slpm, 5 psig of air, and dissolved oxygen maintained at no lower than 50% saturation. When glycerol was depleted, the cells were induced to express glycolate oxidase by growth in the same media except that methanol (50 g) was substituted for glycerol. Glycolate oxidase activity during induction was followed by enzyme assay. After 24 hours of induction the cells were harvested following treatment with glycerol (1 kg). Following harvest the cells were frozen in liquid nitrogen and stored at −80° C.

Unlike *A. nidulans*, *H. polymorpha* and *P. pastoris* cell transformants required permeabilization prior to use as catalyst for the oxidation of glycolic acid to glyoxylic acid. A variety of known methods of permeabilization were useful for preparing cells with sufficient glycolate oxidase activity (see Felix, H. *Anal. Biochemistry*, Vol. 120, 211–234, (1982)); typically, a suspension of 10 wt % wet cells was suspended in a 0.1% (v/v)"TRITON" X-100/20 mM phosphate buffer (pH 7.0) for 15 minutes, then frozen in liquid nitrogen, thawed, and washed with 20 mM phosphate/0.1 mM FMN buffer (pH 7.0).

When using either *H. polymorpha* and *P. pastoris* cell transformants as catalyst for the oxidation of glycolic acid/AMPA mixtures, the addition of soluble *A. niger* catalase was again found to be necessary for the production of high yields of glyoxylic acid. Although the accessible catalase activity of permeabilized cells of *H. polymorpha* or *P. pastoris* was ca. 10-fold greater than that of *A. nidulans*, the endogenous catalase of either methylotrophic yeast was less effective at decomposing byproduct hydrogen peroxide in reaction mixtures containing AMPA than catalase from *A. nidulans* or *A. niger*. Addition of soluble *A. niger* catalase, or permeabilized whole cells of *Saccharomyces cerevisiae* as a supplemental catalase source, resulted in marked improvements in glyoxylic acid production when compared to reactions run in the absence of added catalase.

A fourth microbial cell catalyst which has been utilized in the present invention is a transformant of *Escherichia coli* (a bacteria) which expresses the glycolate oxidase enzyme from spinach, as well as an endogenous catalase. Such an *E. coli* transformant was prepared as described in Macheroux et. al., *Biochem. Biophys. Acta*, Vol. 1132, 11–16 (1992). *E. coli* transformants expressing glycolate oxidase activity were not permeabilized prior to use as catalyst in the present invention. Pertinent portions of the text of the paper by Macheroux et al. is set forth below.

Many of the deficiencies of using soluble enzymes as catalysts in the present application have been eliminated by employing whole microbial cell transformants (either unpermeabilized or permeabilized) as catalyst. Recovery and reuse of the whole-cell catalyst was easily performed by centrifugation or by filtering the catalyst away from the reaction mixture and recycling it to fresh reaction mixture; in this manner, turnover numbers for glycolate oxidase of as high as $10^6$ have been obtained. The ability to bubble oxygen through the reaction mixture without rapidly denaturing the glycolate oxidase (as is observed when using the soluble enzyme) resulted in increases in the reaction rate of at least ten-fold over reactions where the reaction mixture is not bubbled, and this increase in rate significantly reduces the cost of manufacture for this process.

The glycolate oxidase activity (added as whole microbial cell transformant) used in the reaction should be present in an effective concentration, usually a concentration of 0.01 to about 100 IU/mL, preferably about 0.1 to about 10 IU/mL. An IU (International Unit) is defined as the amount of enzyme that will catalyze the transformation of one micromole of substrate per minute. A procedure for the assay of this enzyme is found in I. Zelitch and S. Ochoa, *J. Biol. Chem.*, Vol. 201, 707–718 (1953). This method is also used to assay the activity of recovered or recycled glycolate oxidase. The concentration of catalase should be 50 to 100,000 IU/mL of reaction mixture, preferably 500 to 14,000 IU/mL. It is preferred that both the glycolate oxidase and catalase enzymes be present within the same microbial cell (in the accompanying examples, a transformant of *A. nidulans*, *H. polymorpha*, *P. pastoris*, or *E. coli*). If the concentration of endogenous catalase within the cells is insufficient to efficiently decompose the hydrogen peroxide produced (as in the accompanying examples), an additional source of catalase (e.g., soluble *Aspergillus niger* catalase, or whole cells of *Saccharomyces cerevisiae*) may be added to supplement the endogenous catalase present. Additionally, the catalase and glycolate oxidase concentrations should be adjusted within the above ranges so that the ratio (measured in IU for each) of catalase to glycolate oxidase is at least about 250:1. Flavin mononucleotide (FMN) is an optional added ingredient, used at a concentration of 0.0 to 2.0 mM, preferably 0.01 to 0.2 mM.

In view of the above effective concentration ranges, it should be appreciated that the improved process according to the instant invention encompasses and is intended to cover the use of all microbial cell catalysts, i.e., whole cell catalysts, that express glycolate oxidase and/or catalase in these operative ranges. Thus for purposes of this invention the term whole microbial cell catalyst includes, by way of example but not limited thereto, genetically-engineered microbial transformants of the preferred embodiments and selected strains of either a natural or mutated microbe of enhanced expression capacity and/or mixtures thereof that actually result in effective concentration ranges as set out above.

Glycolic acid (2-hydroxyacetic acid) is available commercially. In the present reaction its initial concentration is in the range of 0.10M to 2.0M, preferably between 0.25M and 1.0M. It can be used as such or as a compatible salt thereof, that is, a salt that is water-soluble and whose cation does not interfere with the desired conversion of glycolic acid to glyoxylic acid, or the subsequent reaction of the glyoxylic acid product with the aminomethylphosphonic acid to form N-(phosphonomethyl)glycine. Suitable and compatible salt-forming cationic groups are readily determined by trial. Representative of such salts are the alkali metal, alkaline earth metal, ammonium, substituted ammonium, phosphonium, and substituted phosphonium salts.

The conversion of glycolic acid to glyoxylic acid is conveniently and preferably conducted in aqueous media. Aminomethylphosphonic acid (AMPA), or a suitable salt thereof, is added to produce a molar ratio of AMPA/glycolic acid (starting amount) in the range of from 0.01/1.0 to 3.0/1.0, preferably from 0.25/1.0 to 1.05/1.0. After combining AMPA and glycolic acid in an aqueous solution, the pH of the resulting mixture is adjusted to a value between 6 and 10, preferably between 7.0 and 8.5. Within this pH range, the exact value may be adjusted to obtain the desired pH by adding any compatible, non-interfering base, including alkali metal hydroxides, carbonates, bicarbonates and phosphates. The pH of the reaction mixture decreases slightly as the reaction proceeds, so it is often useful to start the reaction near the high end of the maximum enzyme activity pH range, about 9.0–8.5, and allow it to drop during the reaction. The pH can optionally be maintained by the separate addition of a non-interfering inorganic or organic buffer, since enzyme activity varies with pH.

It is understood that glycolic and glyoxylic acid are highly dissociated in water, and at pH of between 7 and 10 are largely if not substantially entirely present as glycolate and glyoxylate ions. It will also be appreciated by those skilled in the art that glyoxylic acid (and its conjugate base, the glyoxylate anion) may also be present as the hydrate, e.g. $(HO)_2CHCOOH$ and/or as the hemiacetal, HOOC-CH(OH)OCH(OH)COOH, which compositions and their anionic counterparts are equivalent to glyoxylic acid and its anion for the present purpose of being suitable reactants for N-(phosphonomethyl)glycine formation.

Oxygen ($O_2$), the oxidant for the conversion of the glycolic acid to glyoxylic acid, may be added as a gas to the reaction by agitation of the liquid at the gas-liquid interface, through a membrane permeable to oxygen, or by sparging (bubbling) oxygen through the reaction mixture. It is believed that under most conditions, the reaction rate is at least partially controlled by the rate at which oxygen can be dissolved into the aqueous medium. Thus, although oxygen can be added to the reaction as air, it is preferred to use a relatively pure form of oxygen, and even use elevated pressures. Although no upper limit of oxygen pressure is known, oxygen pressures up to 50 atmospheres may be used, and an upper limit of 15 atmospheres is preferred. Agitation is important to maintaining a high oxygen dissolution (hence reaction) rate. Any convenient form of agitation is useful, such as stirring.

The reaction temperature is an important variable, in that it affects reaction rate and the stability of the enzymes. A reaction temperature of 0° C. to 40° C. may be used, but the preferred reaction temperature range is from 5° C. to 15° C. Operating in the preferred temperature range maximizes recovered enzyme activity at the end of the reaction. The temperature should not be so low that the aqueous solution starts to freeze. Temperature can be controlled by ordinary methods, such as, but not limited to, by using a jacketed reaction vessel and passing liquid of the appropriate temperature through the jacket. The reaction vessel may be constructed of any material that is inert to the reaction ingredients.

Following the cessation of contacting the reaction solution with $O_2$, the microbial cell catalyst may be removed by decantation, filtration or centrifugation and reused. Flavin mononucleotide (FMN) may optionally be removed by contacting the solution with activated carbon. The solution containing glyoxylic acid and aminomethylphosphonic acid (which are believed to be in equilibrium with the corresponding imine), is treated in accordance with any of the processes known to the art for producing N-(phosphonomethyl)glycine.

Catalytic hydrogenation is a preferred method for preparing N-(phosphonomethyl)glycine from a mixture containing glyoxylic acid and aminomethylphosphonic acid. Hydrogenation catalysts suitable for this purpose include (but are not limited to) the various platinum metals, such as iridium, osmium, rhodium, ruthenium, platinum, and palladium; also various other transition metals such as cobalt, copper, nickel and zinc. The catalyst may be unsupported, for example as Raney nickel or platinum oxide; or it may be supported, for example as platinum on carbon, palladium on alumina, or nickel on kieselguhr. Palladium on carbon, nickel on kieselguhr and Raney nickel are preferred. The hydrogenation can be performed at a pH of from 4 to 11, preferably from 5 to 10. The hydrogenation temperature and pressure can vary widely. The temperature is generally in the range of 0° C. to 150° C., preferably from 20° C. to 90° C., while the $H_2$ pressure is generally in the range of from about atmospheric to about 100 atmospheres, preferably from 1 to 10 atmospheres. N-(phosphonomethyl)glycine, useful as a post-emergent herbicide, may be recovered from the reduced solution, whatever the reducing method employed, by any of the recovery methods known to the art.

In the following examples, which serve to further illustrate the invention, the yields of glyoxylate, formate and oxalate, and the recovered yield of glycolate, are percentages based on the total amount of glycolic acid present at the beginning of the reaction. Analyses of reaction mixtures were performed using high pressure liquid chromatography: organic acid analyses were performed using a Bio-Rad HPX-87H column, and AMPA and N-(phosphonomethyl)glycine were analyzed using a Bio-Rad Aminex Glyphosate Analysis column.

Microbial cell transformants were assayed for glycolate oxidase activity by accurately weighing ca. 5–10 mg of the wet cells into a 3-mL quartz cuvette containing a magnetic stirring bar and 2.0 mL of a solution which was 0.12 mM in 2,6-dichlorophenolindophenol (DCIP) and 80 mM in TRIS buffer (pH 8.3). The cuvette was capped with a rubber septum and the solution deoxygenated by bubbling with nitrogen for 5 min. To the cuvette was then added by syringe 40 µL of 1.0M glycolic acid/1.0M TRIS (pH 8.3), and the mixture stirred while measuring the change in absorption with time at 605 nm ($\epsilon$=22,000). Catalase activity was assayed by accurately weighing ca. 2–5 mg of the wet cells into a 3-mL quartz cuvette containing a magnetic stirring bar and 2.0 mL of a distilled water, then adding 1.0 mL of 59 mM hydrogen peroxide in 50 mM phosphate buffer (pH 7.0) and measuring the change in absorption with time at 240 nm ($\epsilon$=39.4). Glycolate oxidase and catalase activities of the *A. nidulans* wet cells (unpermeabilized) cultured in different media ranged from 0.5–4.0 DCIR IU/gram wet cells for glycolate oxidase and 500–7000 IU/gram wet cells for endogenous catalase. Glycolate oxidase and catalase activities of the *H. polymorpha* or *P. pastoris* wet cells (permeabilized) cultured in different media ranged from 20–60 DCIP IU/gram wet cells for glycolate oxidase and 30,000–80,000 IU/gram wet cells for endogenous catalase.

EXAMPLE 1

A 300-mL EZE-Seal stirred autoclave reactor (Autoclave Engineers) was charged with 100 mL of a solution containing glycolic acid (0.500M), aminomethylphosphonic acid (0.375M), isobutyric acid (0.100M, HPLC internal standard), and flavin mononucleotide (0.01 mM) at pH 8.3 (adjusted with 50% NaOH), and the solution cooled to 5° C. To the reactor was then added 26 g of frozen (−80° C.) *Aspergillus nidulans* FT17SYCSL/OL (124 IU glycolate oxidase and 57,800 IU catalase) deposited with the Northern regional Research Laboratories on Sep. 24, 1992, under the terms of the Budapest Treaty and designated by the accession number NRRL 21000 and $1.4 \times 10^6$ units of *Aspergillus niger* soluble catalase (Sigma), the cells allowed to thaw at 5° C., and the pH of the resulting mixture re-adjusted to 8.3 with 50% NaOH. This mixture was stirred at 400 rpm and 5° C. under 120 psig of oxygen while bubbling oxygen through the mixture at 50 mL/min. The reaction was monitored by taking a 0.40 mL aliquot of the reaction mixture at regular intervals, filtering the aliquot using a Millipore "ULTRAFREE"-MC 10,000 NMWL Filter Unit, and analyzing the filtrate by HPLC. After 10 hours, the yields of glyoxylic acid, oxalic acid, and formic acid were 91%, 0%, and 7.9%, respectively, with 2.5% recovery of glycolic acid. The final activities of glycolate oxidase and *Aspergillus niger* catalase were 11% and 87% of their initial values.

EXAMPLE 2 (COMPARATIVE)

The reaction described in Example 1 was repeated, except that the addition of *Aspergillus niger* soluble catalase (Sigma) was omitted. After 22 hours, the yields of glyoxylic acid, oxalic acid, and formic acid were 1.7%, 0%, and 87.4%, respectively, with complete conversion of glycolic acid. There was no detectable glycolate oxidase or catalase activity in the *Aspergillus nidulans* FT17SYCSL/OL cells at the end of the reaction.

EXAMPLE 3

A 300-mL EZE-Seal stirred autoclave reactor (Autoclave Engineers) was charged with 100 mL of a solution containing glycolic acid (0.500M), aminomethylphosphonic acid (0.375M), isobutyric acid (0.100M, HPLC internal standard), and flavin mononucleotide (0.01 mM) at pH 8.3 (adjusted with 50% NaOH), and the solution cooled to 5° C. To the reactor was then added 26 g of frozen (−80° C.) *Aspergillus nidulans* FT17SYCSL/OL (124 IU glycolate oxidase and 57,800 IU catalase) and $5.6 \times 10^5$ units of *Aspergillus niger* soluble catalase (Sigma), the cells allowed to thaw at 5° C., and the pH of the resulting mixture re-adjusted to 8.3 with 50% NaOH. This mixture was stirred at 400 rpm and 5° C. under 120 psig of oxygen while bubbling oxygen through the mixture at 50 mL/min. After 10 hours, the yields of glyoxylic acid, oxalic acid, and formic acid were 83%, 0%, and 9.4%, respectively, with 4.4% recovery of glycolic acid. The final activities of glycolate oxidase and *Aspergillus niger* catalase were 17% and 88% of their initial values.

EXAMPLE 4

A 300-mL EZE-Seal stirred autoclave reactor (Autoclave Engineers) was charged with 100 mL of a solution containing glycolic acid (0.500M), aminomethylphosphonic acid (0.375M), isobutyric acid (0.100M, HPLC internal standard), and flavin mononucleotide (0.01 mM) at pH 8.3 (adjusted with 50% NaOH), and the solution cooled to 5° C. To the reactor was then added 15 g of frozen (−80° C.) *Aspergillus nidulans* FT17SYCSL/OL (72 IU glycolate oxidase and 33,300 IU catalase) and $1.4 \times 10^6$ units of *Aspergillus niger* soluble catalase (Sigma), the cells allowed to thaw at 5° C., and the pH of the resulting mixture re-adjusted to 8.3 with 50% NaOH. This mixture was stirred at 400 rpm and 5° C. under 120 psig of oxygen while bubbling oxygen through the mixture at 50 mL/min. After 17 hours, the yields of glyoxylic acid, oxalic acid, and formic acid were 76%, 0%, and 4.1%, respectively, with 16.8% recovery of glycolic acid. The final activities of glycolate oxidase and *Aspergillus niger* catalase were 7% and 49% of their initial values.

EXAMPLE 5

A 300-mL EZE-Seal stirred autoclave reactor (Autoclave Engineers) was charged with 100 mL of a solution containing glycolic acid (0.500M), aminomethylphosphonic acid (0.375M), isobutyric acid (0.100M, HPLC internal standard), and flavin mononucleotide (0.01 mM) at pH 8.3 (adjusted with 50% NaOH), and the solution cooled to 5° C. Frozen (−80° C.) *Aspergillus nidulans* FT17SYCSL/OL (26 g, 124 IU glycolate oxidase and 57,800 IU catalase) were allowed to thaw at 5° C., then washed with 2×100 mL of $KH_2PO_4$ (50 mM, pH 7.0)/FMN (0.01 mM) buffer at 5° C. and the washed cells added to the reactor with $1.4 \times 10^6$ units of *Aspergillus niger* soluble catalase (Sigma). The pH of the resulting mixture was re-adjusted to 8.3 with 50% NaOH, then stirred at 400 rpm and 5° C. under 120 psig of oxygen while bubbling oxygen through the mixture at 50 mL/min. After 11.5 hours, the yields of glyoxylic acid, oxalic acid, and formic acid were 94%, 3.5%, and 2.7%, respectively, with 1.3% recovery of glycolic acid. The final activities of glycolate oxidase and *Aspergillus niger* catalase were 7% and 77% of their initial values.

EXAMPLE 6

A 300-mL EZE-Seal stirred autoclave reactor (Autoclave Engineers) was charged with 100 mL of a solution containing glycolic acid (0.500M), aminomethylphosphonic acid (0.375M), isobutyric acid (0.100M, HPLC internal standard), and flavin mononucleotide (0.01 mM) at pH 8.3 (adjusted with 50% NaOH), and the solution cooled to 5° C. Freshly-harvested *Aspergillus nidulans* FT17SYCSL/OL (37 g, 44 IU glycolate oxidase and 57,800 IU catalase) were washed with 4×100 mL of $KH_2PO_4$ (50 mM, pH 7.0)/FMN (0.01 mM) buffer at 5° C. and the washed cells added to the reactor with $1.4 \times 10^6$ units of *Aspergillus niger* soluble catalase (Sigma). The pH of the resulting mixture was re-adjusted to 8.3 with 50% NaOH, then stirred at 400 rpm and 5° C. under 120 psig of oxygen while bubbling oxygen through the mixture at 50 mL/min. After 15 hours, the yields of glyoxylic acid, oxalic acid, and formic acid were 84%, 0%, and 9.4%, respectively, with 6.4% recovery of glycolic acid.

At the completion of the reaction, the reaction mixture was centrifuged at 5° C. and the supernatant decanted. The resulting pellet of *Aspergillus nidulans* cells was resuspended in 100 mL of fresh reaction mixture at 5° C., and the reaction repeated under conditions identical to those described above. After 25 hours, the yields of glyoxylic acid, oxalic acid, and formic acid were 59%, 1.1%, and 1.6%, respectively, with 43% recovery of glycolic acid. An assay of glycolate oxidase in the cells at this time indicated no remaining activity.

EXAMPLE 7

A 300-mL EZE-Seal stirred autoclave reactor (Autoclave Engineers) was charged with 100 mL of a solution containing glycolic acid (0.500M), aminomethylphosphonic acid (0.375M), flavin mononucleotide (0.01 mM), and no added HPLC internal standard (pH 8.3, adjusted with 50% NaOH), and the solution cooled to 5° C. Frozen (−80° C.) *Aspergillus nidulans* FT17SYCSL/OL (26 g, 124 IU glycolate oxidase and 57,800 IU catalase) were allowed to thaw at 5° C., then washed with 4×100 mL of $KH_2PO_4$ (50 mM, pH 7.0)/FMN (0.01 mM) buffer at 5° C. and the washed cells added to the reactor with $1.4 \times 10^6$ units of *Aspergillus niger* soluble catalase (Sigma). The resulting mixture was stirred at 400 rpm and 5° C. under 120 psig of oxygen while bubbling oxygen through the mixture at 50 mL/min. After 11 hours, the yields of glyoxylic acid, oxalic acid, and formic acid were 89%, 4.5%, and 2.0%, respectively, with complete conversion of glycolic acid.

EXAMPLE 8

Into a 3 oz. Fischer-Porter glass aerosol reaction vessel was placed a magnetic stirring bar and 10 mL of an aqueous solution containing glycolic acid (0.500M), aminomethylphosphonic acid (0.375M), isobutyric acid (0.100M, HPLC internal standard), and flavin mononucleotide (0.01 mM) at pH 8.3 (adjusted with 50% NaOH), and the solution cooled to 5° C. To the vessel was then added 0.47 g of *Hansenula polymorpha* transformant GO1 (10 IU glycolate oxidase and 22,100 IU catalase) which had been permeabilized by treatment with 0.1% "TRITON" X-100/1 freeze-thaw, and $1.4 \times 10^6$ units of *Aspergillus niger* soluble catalase (Sigma). The pH of the resulting mixture was re-adjusted to 8.3 with 50% NaOH, then the reaction vessel was sealed and the reaction mixture was cooled to 5° C. The vessel was flushed with oxygen by pressurizing to 70 psig and venting to atmospheric pressure five times with stirring, then the vessel was pressurized to 70 psig of oxygen and the mixture stirred at 5° C. Aliquots (0.10 mL) were removed by syringe through a sampling port (without loss of pressure in the vessel) at regular intervals for analysis by HPLC to monitor the progress of the reaction. After 16 hours, the HPLC yields of glyoxylate, formate, and oxalate were 90.1%, 1.3%, and 5.9%, respectively, and 3.0% glycolate remained. The remaining glycolate oxidase activity and total catalase activity were 86% and 136%, respectively, of their initial values.

EXAMPLE 9 (COMPARATIVE)

The reaction in Example 8 was repeated, except that the addition of $1.4 \times 10^6$ units of *Aspergillus niger* soluble catalase (Sigma) was omitted. After 16 hours, the HPLC yields of glyoxylate, formate, and oxalate were 57.6%, 32.5%, and 2.6%, respectively, and 8.9% glycolate remained. The remaining permeabilized cell activity of glycolate oxidase and catalase were 60% and 378%, respectively, of their initial values.

EXAMPLE 10 (COMPARATIVE)

The reaction in Example 8 was repeated, except that 1.67 g of permeabilized (0.1% "TRITON" X-100/1 freeze-thaw) *Saccharomyces cerevisiae* cells having $1.4 \times 10^6$ units of catalase activity were substituted for the addition of $1.4 \times 10^6$ units of *Aspergillus niger* soluble catalase (Sigma). After 16 h, the HPLC yields of glyoxylate, formate, and oxalate were 67.2%, 19.7%, and 6.0%, respectively, and no glycolate remained.

EXAMPLE 11

Into a 3 oz. Fischer-Porter glass aerosol reaction vessel was placed a magnetic stirring bar and 10 mL of an aqueous solution containing glycolic acid (0.500M), aminomethylphosphonic acid (0.375M), isobutyric acid (0.100M, HPLC internal standard), and flavin mononucleotide (0.01 mM) at pH 8.3 (adjusted with 50% NaOH), and the solution cooled to 5° C. To the vessel was then added 0.75 g of a *Pichia pastoris* transformant GS115-MSP10 (13.2 IU glycolate oxidase and 21,200 IU catalase) which had been permeabilized by treatment with 0.1% "TRITON" X-100/1 freeze-thaw. The pH of the resulting mixture was re-adjusted to 8.3 with 50% NaOH, then the reaction vessel was sealed and the reaction mixture was cooled to 5° C. The vessel was flushed with oxygen by pressurizing to 70 psig and venting to atmospheric pressure five times with stirring, then the vessel was pressurized to 70 psig of oxygen and the mixture stirred at 5° C. Aliquots (0.10 mL) were removed by syringe through a sampling port (without loss of pressure in the vessel) at regular intervals for analysis by HPLC to monitor the progress of the reaction. After 16 hours, the HPLC yields of glyoxylate, formate, and oxalate were 30.5%, 59.2%, and 10.7%, respectively, and 0.8% glycolate remained.

EXAMPLE 12

A 300-mL EZE-Seal stirred autoclave reactor equipped with Dispersimax Impeller (Autoclave Engineers) was charged with 100 mL of a solution containing glycolic acid (0.500M), aminomethylphosphonic acid (0.375M), isobutyric acid (0.100M, HPLC internal standard), and flavin mononucleotide (0.01 mM) at pH 8.3 (adjusted with 50% NaOH), and the solution cooled to 5° C. To the reactor was then added 10 g of *Pichia pastoris* transformant, NRRL Y-21001, (391 IU glycolate oxidase and 457,000 IU catalase) which had been permeabilized by treatment with 0.1% "TRITON" X-100/1 freeze-thaw, and $1.4 \times 10^6$ units of *Aspergillus niger* soluble catalase (Sigma). The pH of the resulting mixture re-adjusted to 8.3 with 50% NaOH. This mixture was stirred at 1000 rpm, which bubbled oxygen through the mixture via the action of the turbine impeller, and at 5° C. under 120 psig of oxygen. The reaction was monitored by taking a 0.40 mL aliquot of the reaction mixture at regular intervals, filtering the aliquot using a Millipore "ULTRAFREE"-MC 10,000 NMWL Filter Unit, and analyzing the filtrate by HPLC. After 1.0 hour, the yields of glyoxylic acid, oxalic acid, and formic acid were 89.8%, 6.0%, and 2.9%, respectively, with 1.7% recovery of glycolic acid. The final activities of permeabilized-cell glycolate oxidase and catalase were 117% and 78% of their initial values.

The microbial cell catalyst was recovered from the reaction mixture described above by centrifugation. Without further treatment the cell pellet was mixed with 100 mL of fresh reaction mixture and an additional $1.4 \times 10^6$ units of *Aspergillus niger* soluble catalase, and the reaction repeated. After 1.0 hour, the yields of glyoxylic acid, oxalic acid, and formic acid were 87.8%, 5.0%, and 5.3%, respectively, with 2.9% recovery of glycolic acid. The final activities of permeabilized-cell glycolate oxidase and catalase were 172% and 61% of their initial values.

EXAMPLE 13

The mixture of glyoxylic acid and AMPA produced via the reaction described in Example 2 was centrifuged to remove the *Aspergillus nidulans* whole cell catalyst, then filtered using an Amicon "CENTRIPREP" 10 concentrator (10,000 molecular weight cut-off) to remove the soluble *Aspergillus niger* catalase. The resulting solution was stirred with activated carbon (0.50 g) to remove FMN, filtered, and placed in the 300 mL, 316 SS cup of an Autoclave Engineers EZE-Seal reactor, along with 0.50 g of 10% Pd on activated carbon. The reactor was flushed with nitrogen, then charged with hydrogen at 300 psig and stirred at 1000 rpm and 27° C. After 22 hours, the yield of N-(phosphonomethyl)glycine (based on AMPA) was 80%.

EXAMPLE 14

The mixture of glyoxylic acid and AMPA produced via the reaction described in Example 4 was centrifuged to remove the *Aspergillus nidulans* whole cell catalyst, then filtered using an Amicon "CENTRIPREP" 10 concentrator (10,000 molecular weight cut-off) to remove the soluble *Aspergillus niger* catalase. The resulting solution was stirred with activated carbon (0.50 g) to remove FMN, filtered, and placed in the 300 mL, 316 SS cup of an Autoclave Engineers EZE-Seal reactor, along with 0.50 g of 10% Pd on activated carbon. The reactor was flushed with nitrogen, then charged with hydrogen at 300 psig and stirred at 1000 rpm and 27° C. After 22 hours, the yield of N-(phosphonomethyl)glycine (based on AMPA) was 89%.

EXAMPLE 15

The mixture of glyoxylic acid and AMPA produced via the reaction described in Example 6 was centrifuged to remove the *Aspergillus nidulans* whole cell catalyst, then filtered using an Amicon "CENTRIPREP" 10 concentrator (10,000 molecular weight cut-off) to remove the soluble *Aspergillus niger* catalase. The resulting solution was stirred with activated carbon (0.50 g) to remove FMN, filtered, and placed in a 300 mL glass liner, along with 0.50 g of 10% Pd on activated carbon. The glass liner was sealed in an autoclave and flushed with nitrogen, then charged with hydrogen at 1000 psig and mixed by rocking at 27° C. After 11 hours, the yield of N-(phosphonomethyl)glycine (based on AMPA) was 76%.

EXAMPLE 16

A 300-mL EZE-Seal stirred autoclave reactor equipped with Dispersimax Impeller (Autoclave Engineers) was charged with 100 mL of a solution containing glycolic acid (0.50M), aminomethylphosphonic acid (0.375M), isobutyric acid (0.100M, HPLC internal standard), and flavin mononucleotide (0.01 mM) at pH 8.3, and the solution cooled to 5° C. To the reactor was then added 30 g of *E. coli* transformant (25.2 IU glycolate oxidase and 39,900 IU catalase), and the mixture stirred at 1000 rpm, which bubbled oxygen through the mixture via the action of the turbine impeller, and at 5° C. under 120 psig of oxygen. The reaction was monitored by taking a 0.40 mL aliquot of the reaction mixture at regular intervals, filtering the aliquot using a Millipore Ultrafree-MC 10,000 NMWL Filter Unit, and analyzing the filtrate by HPLC. After 19 hours, the yields of glyoxylic acid, oxalic acid, and formic acid were 8.6%, 8.3%, and 1.1%, respectively, with 57.3% glycolic acid remaining. The recovered activities of microbial glycolate oxidase and catalase were 10% and 68% of their initial values, respectively.

EXAMPLE 17

The reaction described in Example 16 was repeated using a second growth of 30 g of *E. coli* transformant having a higher glycolate oxidase activity (72 IU glycolate oxidase and 29,600 IU catalase). After 23 hours, the yields of glyoxylic acid, oxalic acid, and formic acid were 18.3%, 1.9%, and 2.9%, respectively, with 42.6% glycolic acid remaining. The recovered activities of microbial glycolate oxidase and catalase were 18% and 71% of their initial values, respectively.

The following text is taken from U.S. Ser. No. 08/085,488 entitled "Glycolate Oxidase Production" filed July 1993, which text relates to culturing a transformant of an Aspergillus species containing DNA coding glycolate oxidase. The products serve as biocatalysts in conversion of glycolic acid to glyoxylic acid.

SUMMARY OF THE INVENTION

It is an object of the present invention to provide a novel source of glycolate oxidase.

It is another object of the present invention to provide a novel source of glycolate oxidase and catalase, in a combination suitable for bioconversion processes.

It is another object of the present invention to provide a method of production of a whole-cell microorganism containing glycolate oxidase, and optionally, catalase, for use as a catalyst in the bioconversion of glycolic acid to glyoxylic acid.

According to one aspect of the present invention, there is provided a method for producing glycolate oxidase in enzymatically active form and in relatively high concentration, which comprises the step of culturing an Aspergillus strain having incorporated stably and expressibly therein a heterologous DNA molecule coding for spinach glycolate oxidase or an enzymatically active variant thereof.

According to another aspect of the present invention, there is provided an Aspergillus strain having incorporated stably and expressibly therein a DNA molecule coding for glycolate oxidase or an enzymatically active variant thereof. According to one embodiment of the invention, the glycolate oxidase is spinach glycolate oxidase. According to another embodiment of the invention, the glycolate oxidase is a variant of spinach glycolate oxidase, lacking the peroxisomal signal.

According to another aspect of the present invention, there is provided a process for constructing a microbial source of enzymatically active glycolate oxidase, comprising the step of introducing into an Aspergillus host a recombinant DNA construct having DNA coding for glycolate oxidase linked operably with DNA enabling expression thereof in said Aspergillus host.

In another aspect of the present invention, there is provided a recombinant DNA construct useful for constructing a microbial source of enzymatically active glycolate oxidase, wherein the construct comprises DNA coding for glycolate oxidase or an enzymatically active variant thereof, operably linked with DNA enabling expression thereof in an Aspergillus strain.

The utility of the present invention is as a method of producing a catalyst for use in a process for converting glycolic acid to glyoxylic acid, comprising the step of exposing glycolic acid to mycelia obtained from a glycolate oxidase-producing Aspergillus strain of the present invention.

BRIEF DESCRIPTION OF THE DRAWING

FIG. 1 illustrates the nucleotide sequence and deduced amino acid sequence of spinach cDNA coding for glycolate oxidase.

FIG. 2 illustrates the steps taken to amplify glycolate oxidase-encoding cDNA by polymerase chain reaction.

FIG. 3 illustrates schematically the steps in constructing a recombinant DNA expression construct to achieve production of glycolate oxidase in an Aspergillus host.

DESCRIPTION OF THE PREFERRED EMBODIMENTS

The invention relates to production of enzymatically active glycolate oxidase in relatively high yield by filamentous fungi of the genus Aspergillus.

As used herein, the term "enzymatically active" refers to glycolate oxidase in a form capable of converting glycolate to glyoxylate as determined by assays of conventional design. One particular assay useful to identify enzymatically active glycolate oxidase is that described by Soda, et al., 1973, *Agr. Biol. Chem.*, 37(6):1393. This assay measures the glyoxylate produced by the glycolate oxidase-catalyzed oxidation of glycolate by reacting said glyoxylate with glycine and o-aminobenzaldehyde to form a yellow complex having an absorbance maximum at 440 nm.

The glycolate oxidase of the present invention may have a structure corresponding to any naturally occurring form of the enzyme, or may have a genetically engineered variant structure, provided however that enzymatically active glycolate oxidase, as defined above, is retained. Naturally-occurring forms of glycolate oxidase include, for example, spinach-produced glycolate oxidase. As shown in FIG. 1 herein, spinach glycolate oxidase consists, in its mature form, of 369 amino acid arranged in the sequence shown (FIG. 1). According to a preferred embodiment of the present invention, the glycolate oxidase is spinach glycolate oxidase or an enzymatically active variant of spinach glycolate oxidase, e.g. a enzymatically active fragment of the enzyme, or an analogue in which one or more amino acids is replaced using conservative amino acid replacements, or a variant in which the region of the enzyme which directs its peroxisomal accumulation is deleted (see Macheroux et al., supra, incorporated herein by reference).

The present invention employs as host for glycolate oxidase production any of the species and varieties of the filamentous fungal genus Aspergillus, members of which are characterized by a vegetative mycelium having a cell wall composed of chitin, cellulose, and other complex polysaccharides. As such the *Aspergilli* are morphologically, physiologically and genetically distinct from yeast. Vegetative growth is by hyphal elongation and carbon catabolism is obligately aerobic. Various species of Aspergillus may serve as glycolate oxidase production hosts, in accordance with the present invention. Particularly suitable species include *Aspergillus niger* and the closely related *Aspergillus niger var. awamori, Aspergillus nidulans, Aspergillus oryzae* and *Aspergillus sojae.*

In a preferred embodiment of the invention, the Aspergillus strain serving as host for glycolate oxidase production is pre-selected for its ability to produce relatively higher levels of endogenous catalase activity, as determined by standard catalase activity assays and in accordance with the procedures herein exemplified.

A variety of genetic constructs, adapted to receive heterologous DNA and to control expression thereof, have been developed for use with Aspergillus hosts and any of these may be employed for the purpose of producing glycolate oxidase in the Aspergillus host. Such genetic constructs, conventionally referred to as expression cassettes, comprise a region 5' of the heterologous DNA insert which harbours transcriptional and translational initiation controls, and a region 3' of the DNA insert which controls translational termination and, optionally, transcriptional termination. Both control regions are derived typically from genes homologous to Aspergillus, although it is to be understood that such control regions need not be derived from the genes native to the specific species chosen as glycolate oxidase production host, and need not be derived from the same Aspergillus gene.

Initiation control regions, more commonly referred to as promoters, which are useful to drive expression of glycolate oxidase-encoding DNA include those derived from genes in the ethanol utilization pathway of *Aspergillus nidulans*, including the alcohol dehydrogenase genes alcA, aldA and $ADH_3$ gene. Suitable initiation controls also include those derived from the triose phosphate isomerase genes of *Aspergillus niger* and *Aspergillus nidulans*, the trpC gene of *Aspergillus nidulans*, the amdS gene of *Aspergillus nidulans*, the pectin lyase gene of various Aspergillus species as well as the glucoamylase gene of *Aspergillus niger*, and certain amylase genes of *Aspergillus oryzae.*

Termination control regions, which include a polyadenylation site for translational termination and regions functional to terminate transcription, may also be derived from various genes native to Aspergillus hosts, or optionally other filamentous fungal hosts. Such regions may be derived, for example, from the *Aspergillus niger* glucoamylase gene, the *Aspergillus nidulans* trpC gene and the *Mucor miehei* genes. It has been found that transcriptional termination regions are dispensible, but these may be included if desired. Moreover, an Aspergillus-derived polyadenylation site can be unnecessary, provided that the polyadenylation site native to the chosen glycolate oxidase-encoding DNA is incorporated within the expression cassette.

For intracellular production of glycolate oxidase, DNA coding therefore is linked operably, and through its initiation codon, methionine, to the selected expression control region, such that expression results in the formation of glycolate oxidase-encoding messenger RNA. Alternatively, if production of a glycolate oxidase fusion protein is desired, DNA coding for glycolate oxidase is linked at its 5' end, and via the initiating methionine codon, to the 3' end of the gene encoding the carrier protein. Also, if desired, DNA coding for an enzyme-cleavable linker is incorporated without reading frame disruption, between the oxidase-encoding DNA and the carrier-encoding DNA, so that expression yields a fusion protein from which glycolate oxidase can be liberated by enzyme cleavage. A suitable carrier protein is Aspergillus glucoamylase, and suitable cleavable peptide linkers are those cleavable by ubiquitin hydrolase, kex, factor Xa and the like. An example of the fusion protein approach to protein production is provided by Contreras et al, 1991, *Bio Technology*, 9:378.

Glycolate oxidase may also be produced as a secretion product of the Aspergillus host, which accumulates in the growth-conditioned medium. To achieve secretion, there is incorporated on the expression cassette, between the expression controlling DNA and the oxidase-encoding DNA, and in reading frame with the latter, a DNA sequence that codes for a secretion signal functional in the Aspergillus production host. Such signal sequences may code for signal peptides incorporated on peptides produced naturally by Aspergillus, or another filamentous fungus, such as signal peptides associated with *Aspergillus niger* glucoamylase, *Fusarium cutinase, T. resei* cellobiohydrolase 1, and *A. nidulans* acid phosphatase. A variety of signal sequences foreign to Aspergillus have also been found to function in Aspergillus strains, including signal peptides associated with plant proteins such as wheat-amylase and thaumatin, and human proteins such as tissue plasminogen activator, IgG and GM-CSF. Such foreign signal sequences may also be used to drive secretion of glycolate oxidase in the Aspergillus strain.

Transformants of Aspergillus host which co-express glycolate oxidase and catalase are useful for the manufacture of glyoxylic acid from glycolic acid (hydroxyacetic acid). Although the enzyme-catalyzed reaction of glycolic acid with oxygen has been known for many years, high selectivities (>99%) to glyoxylic acid have not been previously obtained, nor has the oxidation of glycolic acid been performed at concentrations of 0.20M to 2.5M. A previous application, U.S. Ser. No. 07/422,011, filed Oct. 16, 1989, "Production of Glyoxylic Acid from Glycolic Acid", described a process for the enzymatic conversion of glycolic acid to glyoxylic acid in the presence of oxygen, an amine buffer, and the soluble enzymes glycolate oxidase and catalase. This process demonstrated the unexpected synergistic effect of using both catalase (to destroy by-product hydrogen peroxide) and an amine buffer capable of forming a chemical adduct with the glyoxylic acid produced (limiting its further oxidation). Neither the separate addition of catalase or an amine buffer were found to produce the high selectivity observed when both were present, and the almost quantitative yields of glyoxylic acid obtained were more than expected from a simple additive effect of using catalase or amine buffer alone. An improvement to the above process utilizes a whole microbial cell as a catalyst, in place of the soluble enzymes.

The previously-reported use of soluble enzymes as catalysts poses several problems: generally, catalyst recovery for reuse is not easily performed, catalyst stability is not as good as can be obtained with immobilized enzyme systems, and soluble enzymes are not stable to the sparging of the reaction mixture with oxygen (required to increase the rate of oxygen dissolution and, thus, reaction rate). Several transformants of *Aspergillus nidulans* have now been constructed, using genetic engineering techniques commonly known to those skilled in the art, which express the glycolate oxidase from spinach as well as an endogenous catalase. Several advantages are offered by the use of these whole-cell catalysts in the previously described process: 1) the whole-cell catalysts are easily recovered from the reaction mixture at the conclusion of the reaction for reuse, whereas the soluble enzyme is only recovered with great difficulty and loss of activity, 2) they are more stable than the soluble enzyme, both for the number of catalyst turnovers obtained versus the soluble enzyme, as well as for recovered enzyme activity at the conclusion of a reaction, and 3), most importantly, they are stable to reaction conditions where oxygen is sparged into the reaction mixture to increase the rate of oxygen dissolution and reaction rate, where under similar reaction conditions the soluble glycolate oxidase is rapidly denatured.

The *Aspergillus nidulans* transformants were prepared by first cloning the spinach gene which codes for glycolate oxidase, then introducing this gene into a strain of *Aspergillus nidulans* which already produced acceptable levels of the endogenous catalase. The resulting transformants were cultured in various media (minimal or SYG rich media) in shaker flasks or fermenters, and additionally, different agents such as oleic acid (OL), hydroxyacetic acid (HA), or corn steep liquor (CSL) were added to the media to increase levels of expression of glycolate oxidase and/or catalase. The different transformants were then screened by assaying the whole cells (untreated) for catalase and glycolate oxidase activity, and by running reactions with the cells as catalysts for the oxidation of glycolic acid to glyoxylic acid. When used as catalysts for the oxidation of glycolic acid to glyoxylic acid, the whole cells were not pre-treated or permeabilized to increase accessibility of the reaction mixture to the enzymes in the interior of the cells; some permeabilization of the cells may take place, either from exposure to the reaction mixture or any of its components, or by freezing and thawing, which was used to store the whole cell catalysts until needed.

Many of the deficiencies of the soluble enzymes were eliminated by employing whole cells of *A. nidulans* as catalyst. Recovery and reuse of the whole-cell catalyst was easily performed by centrifugation or by filtering the catalyst away from the reaction mixture and recycling it to fresh reaction mixture; in this manner, turnovers (i.e., the number of substrate molecules that are converted to product molecule per enzyme catalyst molecule before inactivation of the enzyme) for glycolate oxidase of as high as $10^6$ have been obtained. The ability to bubble oxygen through the reaction mixture without denaturing the enzyme catalyst (as is observed when using the soluble enzyme) resulted in increases in the reaction rate of at least ten-fold over reactions where the reaction mixture is not bubbled, and this increase in rate significantly reduces the cost of manufacture for this process.

EXAMPLE 1

Aspergillus Host Strain Selection

As a preliminary step in the construction of a glycolate oxidase-producing Aspergillus strain, available host strains were examined for endogenous levels of catalase activity, and the strain exhibiting highest catalase activiity was selected to serve as expression host.

In particular, catalase activity was examined in both an argB *Aspergillus niger* strain 350.52 (ATCC 20739), and an *Aspergillus nidulans* strain T580, which is pyr⁻ and harbors multiple copies of the alcR gene. Cultures of each host strain were grown at the 10 liter scale for 48 hours in either minimal medium or rich (SYG) medium (salts, yeast extract, glucose) under inducing conditions. For the *A. nidulans* strains T580, this entailed growth in 3% SYG (with 3% glucose) until glucose levels were minimal, after which the medium was supplemented with the inducer methylethylketone. Mycelia (500–700 g) was harvested 16–20 hours after induction. The *A. niger* strain was grown in SY medium (salts, yeast extract) containing 2% corn starch for 40 hours.

An aliquot (100 mL) of each sample was disrupted with glass beads (0.5 mm) in a DyanoMill vessl for 120 sec, and the refrigerated disruptate was then assayed for catalase activity, using an assay of conventional design, Beers et al., 1952, *J. Biol. Chem.*, 195:133. Results revealed that the catalase levels in the *A. nidulans* host strain T580 were 110 IU/mg. Catalase levels in the *A. niger* strain were found to be 90 IU/mg. On this basis, the *A. nidulans* strain was selected to serve as glycolate oxidase production host.

EXAMPLE 2

Isolation of cDNA Coding for Spinach Glycolate Oxidase

For expression in an Aspergillus species host, DNA coding for spinach glycolate oxidase was first isolated from a library of spinach cDNA. More particularly, poly(A)-containing mRNA was collected from fresh, young spinach leaves using the phenol extraction method and protocols conventional thereto. Complementary DNA was then prepared against the mRNA using the reverse transcriptase-based method and standard protocols.

Based on knowledge of the cDNA sequence coding for spinach glycolate oxidase, as reported by Volokita and Somerville, 1987, *J. Biol. Chem.,* 262(33):15825, the polymerase chain reaction (PCR) approach was used to amplify selectively the glycolate oxidase-encoding DNA resident in the library. In particular, and as shown schematically in FIG. 2, glycolate oxidase-encoding cDNA was amplified in three ligatable sections, using oligonucleotide primers specific for the following regions of the target cDNA; (1) a 203 bp N-terminal region encompassing the ATG initiation codon and including the BglII site 203 bp 3' thereof; (2) a 565 bp central region encompassing the BglII site and including the SacI site; and (3) a 342 bp C-terminal region encompassing the SacI site and the stop codon TAA. As will be noted in FIG. 2, cloning and assembly of the intact coding region was facilitated by the use of primers having non-hybridizing 5' flanks which incorporated a selected restriction site (denoted using the conventional single letter, restriction site designation). Protocols conventional to polymerase chain reaction were employed.

PCR-amplified regions of the cDNA were sequence-verified and assembled into the vector pTZ19R, using the strategy shown in FIG. 2. The correct sequence in the assembled construct was also confirmed.

For Aspergillus strain construction, cDNA coding for spinach glycolate oxidase, obtained as just described, was linked operably with the expression controlling region of the alcohol dehydrogenase I (alcA) gene of *Aspergillus nidulans*, using the strategy illustrated schematically in FIG. 3. The particular vector chosen, designated pTAwtS, is described by Gwynne et al., 1989, *Biochem. Soc. Transactions,* 17:338, which is incorporated herein by reference. Briefly, this vector incorporates, in a pUC8 background, a 2.2 kb HindIII fragment of the *A. nidulans* alcA gene which incorporates all DNA elements required for proper translation and regulated transcription of protein-encoding DNA linked downstream thereof. The particular vector pTAwtS incorporates an engineered NcoI site precisely at the initiation codon downstream of the expression controlling region, to accept in proper translational reading frame a DNA molecule coding for the protein of interest. The vector pTAwtS was further modified by incorporation at a site downstream of the cloning site, a transcriptional terminator derived from the *Aspergillus niger* glucoamylase gene (gla), in the form of a 2.2 kb EcoRI/EcoRI DNA fragment. Thus, as shown in FIG. 3, the intact cDNA clone coding for spinach glycolate oxidase, was incorporated as a BglII/EcoRI fragment into NcoI/EcoRI-cleaved pTAwtS to form pTAwtS-GOD. The transcriptional terminator was then introduced into the EcoRI site 3' of the stop codon resident in the glycolate oxidase coding region to yield pTAwtS-GOD-T. Sequencing across restriction site junctions confirmed taht the construct contained the desired functional components in the proper relationship.

For expression, there was selected as host a strain of *Aspergillus nidulans* designated T580, which is pyr⁻ and harbors multiple copies of the gene alcR, the expression product of which co-regulates expression from the alcA promoter. Construction of the T580 host, from the pyr⁻ *A. nidulans* strain was achieved as described by Felenbok et al., 1988, *Gene,* 73:385, which is incorporated herein by reference. The plasmid pTAwtS-GOD-T was introduced into T580 using now conventional DNA-mediated transformation protocols, described for example by Yelton et al., 1984, *Proc. Natl. Acad. Sci.,* 81:1470. Briefly, spheroplasts of the host strain T580 were first prepared using the cell wall degrading enzyme Novozyme 234. Spheroplasts were then incubated in the presence of calcium/polyethylene glycol, with about 10 ug of pTAwtS-GOD-T and 2 ug of a marker plasmid carrying the pyr4 gene of *Neurospora crassa*. After plating on medium lacking uridine, transformants (about 20 in all) were selected and then subjected to Southern blot analysis by probing with radiolabelled glycolate oxidase-encoding DNA, to confirm the presence of genomically integrated DNA coding for glycolate oxidase. Southern blot analysis revealed that about 80% of the transformants harboured mutiple copies of the spinach glycolate oxidase encoding gene.

Transformants harboring multiple copies of the glycolate oxidase gene were then evaluated individually for glycolate oxidase activity. This was done by introducing conidial inoculum prepared from individual transformants into 50 mL of minimal fungal medium which contains salts and 0.2% fructose/1% threonine (as inducer) combination. After culturing at 30° C. for 48 hours, cell extracts were analyzed for glycolate oxidase activity, using the o-aminobenzaldehyde assay (Soda et al.; see above). In this assay, with absorbance monitoring at 440 nm, several of the transformants tested positive for glycolate oxidase activity, and one transformant, designated *Aspergillus nidulans* strain T17 was selected.

A sample of *Aspergillus nidulans* strain T17, harboring multiple copies of the spinach glycolate oxidase-encoding DNA under expression control of the *A. nidulans* alcA promoter, and mutiple copies of the *A. nidulans* alkR gene, the product of which regulates function of the alcA promoter, was deposited under the terms of the Budapest Treaty with the Northern Regional Research Center, Peoria, Ill., U.S.A. on Sep. 24, 1992, under NRRL No. 21000.

EXAMPLE 3

Expression of a Glycolate Oxidase without the Peroxisomal Targeting Sequence in *Aspergillus nidulans*

A second construct of the glycolate oxidas gene without the peroxisomal targeting sequence Ala-Lys-Leu-COOH (Gould et al., 1990, *EMBO J.* 9:85) was made in an identical manner to that in Example 2 except the (3) PCR fragment was lacking the DNA sequence GCCAGATTA resulting in a 333 bp C-terminal region encompassing the SacI site and the stop codon TAA. Protocols identical to Examples 2 for vector construction and transformation of *Aspergillus nidulans*, but employing this DNA construct, resulted in several strains which tested positive for active glycolate oxidase activity. One of these was selected and designated *Aspergillus nidulans* strain T15.

EXAMPLE 4

Supplements to Fermentaion Media for Increased Expression of Glycolate Oxidase and Catalase In a manner analogous to the evaluation for glycolate oxidase of Examples 2 and 3, the addition of optional additives to the fermentation media was found to increase the levels of glycolate oxidase and/or catalase. Thus the addition of 0.2% oleic acid to SYG media was found to increase the level of glycolate oxidase activity from about 28 IU to 60 IU per gram of cells (dry weight). The addition of 0.5–2% corn steep liquor to this further increased the glycolate oxidase activity to 150–200 IU/g cells (dry weight). The addition of hydroxyacetic acid (0.5 or 1.0%) to SYG, 0.2% oleic acid resulted in increases of catalase activity from 5,400 IU/g (cell dry weight) to 12,700 and 14,000 IU/g (cell dry weight) respectively.

EXAMPLE 5

Bioconversion of Glycolic Acid to Glyoxylic Acid

A 300-mL EZE-Seal stirred autoclave reactor (Autoclave Engineers) was charged with 100 mL of a solution containing glycolic acid (0.75M), ethylenediamine (0.86M, pH 9.0), propionic acid (0.075M, HPLC internal standard), and flavin mononucleotide (0.01 mM), and the solution cooled to 5° C. To the reactor was then added 26 g of frozen (−80° C.) *Aspergillus nidulans* FT17SYG/OL (24 IU glycolate oxidase and 192,000 IU catalase), and the cells allowed to thaw at 5° C. The resulting mixture was stirred at 400 rpm and 5° C. under 120 psig of oxygen, while bubbling oxygen through the mixture at 50 mL/min. The reaction was monitored by taking a 100 mL aliquot of the reaction mixture at regular intervals, mixing the aliquot with 300 mL of 0.1N sulfuric acid to quench the reaction, filtering the aliquot and analyzing by high pressure liquid chromatography. After 11.5 hours, the yields of glyoxylic acid, oxalic acid, and formic acid were 98%, 0%, and 0%, respectively, with complete conversion of glycolic acid. The final activities of glycolate oxidase and catalase were 100% and 62% of their initial values.

EXAMPLE 6 (COMPARATIVE)

Attempted Expession of Glycolate Oxidase in *E. coli*

The design and execution of the experiment was basically as has been described (Goloubinoff et al., 1989, *Nature*, 337: 44). Competent cells of *E. coli*, strain HB101, harboring the plasmid pGO4 encoding the gene for spinach glycolate oxidase and an ampicillin resistance marker, were transformed with the plasmid pGroESL, encoding the genes of the groEL and groES proteins and a chloramphenicol resistance marker, or with the plasmid pTG10, the vector which contains only the chloramphenical resistance marker. The cells were plated out on both antibiotics. Colonies, i.e. double transformants, which were presumed to contain both plasmids, were selected and grown up overnight in liquid culture (2YT) in the presence of both antibiotics. The cells were harvested, washed and lysed. Following centrifugation to remove insoluble material, the supernatant solution was tested for glycolate oxidase activity.

The overexpression of spinach glycolate oxidase in *E. coli* gave only insoluble material and no soluble active enzyme. Using the plasmid pGroESL, which causes the overexpression of the molecular chaperones, and which is know by those skilled in the art to overcome this problem in other cases, did not result in the detection of glycolate oxidase activity in these doubly transformed cells.

---

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 369 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:1:

```
Met  Glu  Ile  Thr  Asn  Val  Asn  Glu  Tyr  Glu  Ala  Ile  Ala  Lys  Gln  Lys
 1                  5                      10                      15

Leu  Pro  Lys  Met  Val  Tyr  Asp  Tyr  Tyr  Ala  Ser  Gly  Ala  Glu  Asp  Gln
               20                      25                      30

Trp  Thr  Leu  Ala  Glu  Asn  Arg  Asn  Ala  Phe  Ser  Arg  Ile  Leu  Phe  Arg
          35                      40                      45

Pro  Arg  Ile  Leu  Ile  Asp  Val  Thr  Asn  Ile  Asp  Met  Thr  Thr  Thr  Ile
     50                      55                      60

Leu  Gly  Phe  Lys  Ile  Ser  Met  Pro  Ile  Met  Ile  Ala  Pro  Thr  Ala  Met
65                       70                      75                      80

Gln  Lys  Met  Ala  His  Pro  Glu  Gly  Glu  Tyr  Ala  Thr  Ala  Arg  Ala  Ala
                    85                      90                      95

Ser  Ala  Ala  Gly  Thr  Ile  Met  Thr  Leu  Ser  Ser  Trp  Ala  Thr  Ser  Ser
               100                     105                     110

Val  Glu  Glu  Val  Ala  Ser  Thr  Gly  Pro  Gly  Ile  Arg  Phe  Phe  Gln  Leu
          115                     120                     125

Tyr  Val  Tyr  Lys  Asp  Arg  Asn  Val  Val  Ala  Gln  Leu  Val  Arg  Arg  Ala
```

```
                    130                          135                             140
Glu  Arg  Ala  Gly  Phe  Lys  Ala  Ile  Ala  Leu  Thr  Val  Asp  Thr  Pro  Arg
145                      150                     155                          160

Leu  Gly  Arg  Arg  Glu  Ala  Asp  Ile  Lys  Asn  Arg  Phe  Val  Leu  Pro  Pro
                    165                     170                          175

Phe  Leu  Thr  Leu  Lys  Asn  Phe  Glu  Gly  Ile  Asp  Leu  Gly  Lys  Met  Asp
               180                      185                     190

Lys  Ala  Asn  Asp  Ser  Gly  Leu  Ser  Ser  Tyr  Val  Ala  Gly  Gln  Ile  Asp
          195                     200                          205

Arg  Ser  Leu  Ser  Trp  Lys  Asp  Val  Ala  Trp  Leu  Gln  Thr  Ile  Thr  Ser
     210                     215                          220

Leu  Pro  Ile  Leu  Val  Lys  Gly  Val  Ile  Thr  Ala  Glu  Asp  Ala  Arg  Leu
225                      230                     235                          240

Ala  Val  Gln  His  Gly  Ala  Ala  Gly  Ile  Ile  Val  Ser  Asn  His  Gly  Ala
               245                          250                     255

Arg  Gln  Leu  Asp  Tyr  Val  Pro  Ala  Thr  Ile  Met  Ala  Leu  Glu  Glu  Val
               260                     265                     270

Val  Lys  Ala  Ala  Gln  Gly  Arg  Ile  Pro  Val  Phe  Leu  Asp  Gly  Gly  Val
          275                     280                     285

Arg  Arg  Gly  Thr  Asp  Val  Phe  Lys  Ala  Leu  Ala  Leu  Gly  Ala  Ala  Gly
     290                     295                     300

Val  Phe  Ile  Gly  Arg  Pro  Val  Val  Phe  Ser  Leu  Ala  Ala  Glu  Gly  Glu
305                     310                     315                          320

Ala  Gly  Val  Lys  Lys  Val  Leu  Gln  Met  Met  Arg  Asp  Glu  Phe  Glu  Leu
               325                     330                          335

Thr  Met  Ala  Leu  Ser  Gly  Cys  Arg  Ser  Leu  Lys  Glu  Ile  Ser  Arg  Ser
               340                     345                     350

His  Ile  Ala  Ala  Asp  Trp  Asp  Gly  Pro  Ser  Ser  Arg  Ala  Val  Ala  Arg
          355                     360                     365

Leu
```

The following are pertinent parts of text found in *Biochimica et Biophysica Acta* 1132(1992) 11–16, "Direct expression of active spinach glycolate oxidase in *Escherichia coli*", by P. Macheroux, S. Mulrooney, C. Williams, Jr., and V. Massey.

INTRODUCTION

Spinach glycolate oxidase (GAO) has been the subject of intensive studies which led to the determination of the active site structure [1]. Recently, the spinach glycolate oxidase gene was cloned by Volokita and Somerville [2]. Therefore, spinach glycolate oxidase became a prime candidate among flavoprotein oxidases to investigate the role of the amino acid resides in the active site by using site-directed mutagenesis. Unfortunately, glycolate oxidase expressed as a β-galactosidase fusion protein was completely insoluble and hence inactive (Volokita and Somerville, personal communication). Marston [3] has recently noted in a review that most eucaryotic polypeptides expressed as fusion proteins in *Escherichia coli* are insoluble. However, attempts to express glycolate oxidase directly, under the control of the heat-inducible APL promoter, also gave rise to an inactive protein which was found to have a lower molecular weight (S öderlind and Lindqvist, personal communication). In both cases the protein was expressed in large quantities (~20 mg/l of cell culture).

Recently, we reported the expression of active glycolate oxidase in *Saccharomyces cererisiae* [4]. This expression is under the control of the constitutive $ADH_1$ promoter and the yield of the target protein is very low, amounting to approx. 0.07% of the total soluble protein fraction [4]. Although this was sufficient to characterize the basic properties of the enzyme it was clearly desirable to obtain larger quantities. Moreover, it was observed that the yield with some genetically engineered mutants was drastically reduced and we were unable to isolate enough material to characterize their physico-chemical properties.

Heterologous proteins have been successfully expressed in *E. coli* using the 17 RNA polymerase expression system developed by Studier and his coworkers [5]. Therefore, we cloned the gene of spinach glycolate oxidase into such an expression system. With this sytem we achieved overexpression of soluble, active glycolate oxidase in *E. coli* which will enable us to study more readily active site mutants of the protein. In this paper we describe the construction of the new recombinant plasmid, demonstrate the identity of the enzyme expressed in *E. coli* with that from year and characterize the conditions under which maximal yields of enzyme are obtained.

MATERIALS AND METHODS

Materials

Restriction enzymes. NcoI and PstI were from Bethesda Research Laboratories, Gaithersburg, Md. (BRL). BamHI and EcoRI were from Toyobo, Japan and BclI was from Boehringer, Indianapolis, Ind.

Antibiotics. Ampicillin, kanamycin and chloramphenicol were from Sigma, St. Louis, Mo.

Growth media. Yeast extract and bacto-tryptone were from Difco, Detroit, Mich., Glycerol (NB grade) was from Boehringer.

Other enzymes. T4 DNA ligase was from BR1, and horseradish peroxidase was from Sigma. Sequenase was obtained from US Biochemicals, Cleveland, Ohio.

Chemicals, o-Dianisidine, flavin mononucleotide (FMN), isopropal-β-D-thiogalactopyranoside (IPTG) and phneyl-methanesulfonyl fluoride (PMSF) were from Sigma. Glycolic acid was from Aldrich, St. Louis, Mo.

Methods

Construction of the expression plasmid. All restriction enzyme digestions, ligations and other common DNA manipulations, unless otherwise stated, were performed by standard procedures [6]. The cDNA clone of glycolate oxidase (GAO) contained in plasmid pGAO [4] was recovered by digestion with EcoRI and subsequent isolation of the small 1400 bp fragment by agarose electrophoresis (1%) and electroblotting on DEAL cellulose (Schleicher & Schült, NA 45. The GAO gene was then cloned into the EcoRI site of plasmid (+) pBluescript (Stratagene, La Jolla, Calif.) and the orientation of the inserted gene was checked by digestion with PsiI. In order to clone the GAO gene into the expression plasmid pET-3d it was necessary to introduce NcoI and BclI restriction sites at the 5' and 3' ends, respectively. The two oligonucleotides used for the directed mutagenesis are shown in FIG. 1. The mutagenesis was performed with the Amersham mutagenesis system, version 2 (Amersham Corporation, Arlington Heights, Ill.) and all steps were carried out as described in the protocol. The two silent mutations were introduced in two consecutive mutagensis experiments. The sequence of the entire gene was then verified by single-strand dideoxy sequencing using the Sequenase sequencing system (USB, Cleveland, Ohio). The plasmid, isolated by E. coli strain GM119 [7], was then digested with BclI and partially with NcoI; the 1150 bp fragment, containing the full length sequence of the GAO gene, was isolated as described above. Plasmid pET-3d was digested with NcoI and BamHI and the large fragment was isolated and purified in the same way. The silently mutated GAO gene was now inserted into the NcoI-BamHI restriction fragment of the expression vector using T4 DNA ligase. The strategy used to clone the GAO gene into the T7 RNA polymerase expression vector is outlined in FIG. 2.

Microbiological manipulations. TB-medium [6] was used for all bacterial cultures. Where required ampicillin (100 µg/ml) and chloramphenicol (50 µg/ml) were added. Plasmid pBluescript was propagated in E. coli strain XL1:blue [8] or strain GM119. Strain IIMS174 was used to propagate plasmid pPM1 and strain BL21 (DE3)/pLsyS [5] was used for expression of the spinach glycolate oxidase. All necessary transformations were carried out with the calcium chloride method as described in the literature [6]. Single-strand DNA for sequencing and the mutagenesis experiments was produced by infecting XL1:blue transformants with the helper phage M13KO7 using standard procedures [6].

Purification of GAO derived from E. coli. Cells from a 1 l growth were harvested by centrifugation at 20000×g for 20 min and the pellet was resuspended in 30 ml 0.1M Tris buffer (pH 8), containing 1 mM EDTA, 0.5 mM FMN and 0.5 mM PMSF. The cells were immediately frozen and stored at −20° C. for at least 15 h and then thawed. Due to the presence of lysozyme in the cells, freezing and thawing was an efficient method of achieving complete lysis. The viscosity of the resulting lysate, owing to the presence of uncleaved DNA, was reduced by adding DNase to a final concentration of 3 µg/ml and incubated for 60 min at 25° C. This crude extract was centrifuged at 40000×g for 30 min and the supernatent decanted and dialyzed against three changes of 1 1 5 mM Tris buffer (pH 8.3), containing 1 mM EDTA. The enzyme was then purified on hydroxyapatide and Q-sepharose as described previoulsy [4]. Details of a tpyical preparation are summarized in Table I.

TABLE I

Purification of spinach glycolate oxidase expressed in Escherichia coli

| Purification step | Volume (ml) | Protein content[b] (mg/ml) | Activity[c] (ΔOD/min) | Specific activity (Δ/min × $OD_{280}$) | Yield (%) | Purification (n-fold) |
|---|---|---|---|---|---|---|
| Crude extract[a] | 35 | 27.5 | 0.18 | 0.007 | 100 | 1 |
| Dialysis | 40 | 24 | 0.15 | 0.00625 | 95 | 0.9 |
| Hydroxyapatite (pool) | 18 | 3.36 | 0.234 | 0.066 | 67 | 10 |
| O sepharose (pool) | 1.5 | 0.73 | 2.2 | 3 | 52 | 430 |

[a]Crude extract was prepared from 14 g of sells, Expression of GAO was induced at $OD_{600}$−1 and cells were harvested after 4 h.
[b]Protein concentration was estimated by assuming that an $OD_{280}$ of 1 equals 1 mg/ml protein.
[c]Acticity was determined by using the enzyme coupled assay described in Materials and Methods Enzyme assay. Glycolate oxidase activity was measured in an enzyme-coupled assay using horseradish peroxidase and o-dianisidine to utilize hydrogen peroxide generated during oxidation of glycolate. A typical assay mixture contained 10 µl of horseradish peroxidase (1 mg/ml), 50 µl of o-dianisidine solution (8 mM, 20% Triton X-1000, 10 µl of 1M sodium glycolate, and 930 µl of 0.1M potassium phosphate buffer (pH 8.3). The reaction was started by adding 10 µl of the glycolate oxidase sample. Formation of the o-dianisidine radical cation ($F_{440}$ - $11600M^{-1}$ $cm^{-1}$), which reflects the catalytic activity of glycolate oxidase, was monitored at 440 nm and at 25° C.

Amino acid sequence determination. N-terminal sequence determination was performed with an Applied Biosystems 470 gas-phasae sequanator, and carried out by the Protein Sequence Facility, University of Michigan.

RESULTS AND DISCUSSION

Expression of Spinach Glycolate Oxidase in *E. coli*

Spinach glycolate oxidase is expressed in *E. coli* in a soluble and active form using the T7 DNA polymerase directed expression system described by Studier and coworkers [5]. Upon induction of the expression system with IPTG the enzyme could be detected on SDS-polyacrylamide gel electrophoesis (FIG. 3) as well as by its enzymatic activity. Since expression of heterologous proteins in *E. coli* frequently yields insoluble protein (inclusion bodies) (see, for example, Ref. 9) we compared the proteins of the supernatant with the proteins of the pellet by SDS-gel electrophoresis (data not shown). From this comparison it was obvious that most if not all of the expressed GAO was contained in the supernatant, i.e., it is soluble.

Identity of Spinach Glycolate Oxidase from Different Expression Systems

GAO expressed in *E. coli* could be purified using the same procedure that was described for spinach GAO expressed in *Saccharomyces cerevisiae* [4]. In both chromatographic steps the enzyme expressed in *E. coli* exhibited the same binding properties as the enzyme expressed in yeast (see Table II). After homogeneity was achieved the specific activity of the *E. coli*-derived enzyme was nearly the same as that observed for enzyme derived from yeast. Table II gives a comparison of the $K_m$-values for glycolate and the specific activities of glycolate oxidases purified from varoius sources. The $K_m$ values compiled in Table II are all in a narrow range (between 0.2 and 0.38 mM). With the exception of the value of the specific activity reported for glycolate oxidase isolated from spinach [11] the specific activities found for the recombinant spinach enzymes are similar to those found for the enzyme from pea leaves [12] and pumpkin cotyledones [13].

The ultraviolte-visible spectrum of recombinant GAO from both sources was identical (data not shown). Although these findings indicate that the enzumes expressed in *E. coli* and in yeast are identical, we were concerned about a recent report [14] that flavocytochrome $b_2$ is expressed in *E. coli* as a somewhat smaller portion lacking the first five N-terminal amino acids. Since GAO is closely related to flavocytochrome $b_2$ (up to 40% sequence identity, Ref. 15) we found it important to make sure that no such truncation occurs with GAO. Furthermore, Söderlind and Lindqvist (personal communication) attempted to express GAO under the control of the APL promoter in *E. coli* but observed that a substantially smaller protein was produced. SDS gel electrophoretic comparison of GAO isolated from *E. coli* and yeast, respectively, did not reveal any differences in apparent molecular weight but since small changes cannot be detected with that method we subjected a purified sample of GAO derived from *E. coli* to an N-terminal protein sequence determination. The result showed that the first ten amino cids of GAO derived from *E. coli* matched the N-terminal sequence determined for the spinach enzyme [2, 16]. Black et al. [14] suggested that the expression of a truncated flavocytochrome $b_2$ is due to translation initiation at a putative Shine-Delgarno sequence that comprises the first amino acid of the mature protein. In contrast to the expression plasmid used for flavocytochrome $b_2$, pPM1 (see FIG. 2) provides an optimal Shine-Delgarno sequence with the right spacing tothe ATG-starting codon of the GAO-gene, which probably prevents formation of fortuitous complexes between the mRNA of GAO and the 16S rRNA.

TABLE III

Expression of glycolate oxidase as a function of time
1 l TB medium containing 100 µg/ml ampicilling and
50 µg/ml cloramphenicol was inoculated with BL21 (DE3)
carrying plasmids pLysS and pPM1. Expression of GAO was
induced with IPTG (final concentartion 400 µM) at an
$OD_{600}$ of 0.8. At the times given below 100 ml samples
were taken and a crude extract was prepared as descriged
in Materials and Methods. GAO activity was determined
in the crude extract employing the enzyme coupled assay
(see Materials and Methods) and the absorbance at 280 nm
was used as a measure of protein concentration.

| Time (h) | Specific activity × $10^{-3}$ ($\Delta OD_{440}$ × min $1/OD_{280}$) |
|---|---|
| 2 | 0.5 |
| 4 | 0.9 |
| 7 | 2.2 |
| 10 | 2.6 |
| 13 | 3.3 |
| 19 | 3.6 |
| 22 | 3.3 |

TABLE II

Comparison of Km values and specific activities of glycolate oxidase isolated from various sources
Values were taken from the following publications: 10, Zeltich and Ochano, 1953; 11, Frigerio and
Harbury, 1958; 12, Kerr and Groves, 1975; 13, Nishimura et al., 1983

|  | Spinach GAO | Yeast-derived spinach GAO | *E. coli*-derived spinach GAO | Pea leaves GAO | Pumpkin cotyledon GAO |
|---|---|---|---|---|---|
| $K_m$ for glycolate[a] (mM) | 0.38 (30° C.)[10] | 0.25 (25° C.) | 0.2 (25° C.) | 0.25 (30° C.)[12] | 0.33 (35° C.)[13] |
| Specific activity (m mol/min per mg) | 9.6 (30° C.)[11] | 31 (25° C.) | 26 (25° C.) | 30 (30° C.)[12] | 40 (35° C.)[13] |

[a]All $K_m$ values reported here were determined at air saturation

Optimization of Growth Conditions

FIG. 3 suggests that GAO might accumulate for more than 4 h after induction, as was also reported for other proteins [5]. In order to determine the optimal time of induction we measured the enzymatic activity over 22 h after addition of IPTG (final concentration 400 µM). The results are summarized in Table III. The enzyme activity inreases steadily with the time of growth after induction with IPTG and reaches a maximum after approx. 18–20 h. This finding implies that the GAO is not toxic for the cells since pladmis which produce toxic gene products are eliminated readily within a few generations of bacterial growth. On the other hand the expression of GAO is low compared to other proteins which have been produced by this expression system to as much as 50% of the total soluble protein [17].

The reasons for this broad range of expression levels are still not fully understood. The possible factors involved have been summarized recently [18].

Another factor which might affect the expressionis the concentration of the inducer. Studier and coworkers [5] used 400 µM IPTG in their protocol. Since IPTG is a rather costly component we decided to investigate the dependency of the expression system on the IPTG concentration. We found that in the range of 25 to 400 µM final concentration of PITG expression level was independent of the inducer concentration.

In order to further optimize the conditions for expression we induced the bacterial cultures are various cell densities. After 2 and 4 h of induction, respectively, the activity and specific activity was measured. Induction of the culture at a low cell density ($OD_{600}$ of 0.2) completely failed to turn on the expression of GAO. At higher cell densities ($OD_{600}$=0.6 and 1.0) expression occurred and was highest at $OD_{600}$=1. At the same time the specific activity was also optimal at $OD_{600}$=1. A summary of this experiment is given in Table IV. After induction of a culture at $OD_{600}$=1 and growth for ~1 18–20 h (see above) GAO accounts for ~1% of the soluble protein.

In comparison with the expression of GAO as a β-galactosidase fusion protein and the expression with the heat inducible APL promoter the yield achieved here was considerably lower. However, in contrast, the newly constructed expression plasmid pPM1 provides soluble and active GAO in amounts sufficient for further physicochemical and rapid reaction investigations of wild-type and mutant glycolate oxidases.

TABLE IV

Induction of glycolate oxidase expression as a function of cell density Three flask each with 1 l TB medium containing 100 µg/ml ampicillin and 50 µg/ml chloroamphenicol were incoluated with BL21 (DE3) carrying plasmidds pLysS and pPMI. At $OD_{600}$ of 0.2, 0.6 and 1.0, respectively, expression of GAO was induced with IPTG (final concentration 400 µM). After 2 and 4 h 100 ml samples were taken and crude extracts were prepared as described in Materials and Methods. GAO activity in the crude extrct was determined with the enzyme coupled assay (see Materials and Methods) and the $OD_{280}$ was used as an estimate for protein concentration.

| Induction at $OD_{600}$ | Induction (h) | Activity ($\Delta OD \times min^1$) | Specific Activity at $10^3$ ($\Delta OD \times min^{-1}/OD_{280}$) |
|---|---|---|---|
| 0.2 | 2 | 0 | — |
|  | 4 | 0 | — |
| 0.6 | 2 | 0.024 | 0.42 |
|  | 4 | 0.045 | 0.97 |
| 1.0 | 2 | 0.170 | 3.2 |
|  | 4 | 0.335 | 5.8 |

ACKNOWLEDGEMENTS

This work [that of Macheroux et al.] was supported by grants from the United States Health Service GM-11106 to V.M., GM-21444 to C.H.W. and by the Health Services and Resarech Administration of the Department of Veteran Affairs. We would like to thank Dennis J. Thiele and Kazuyo Saito for their advice in developing a suitable cloning strategy and their help in the initial stages of the experiments.

REFERENCES

1 Linqvist, Y. and Branden, C.-l. (1989) J. Biol. Chem., 264, 3624–3628.
2 Volokita, M. and Somerville, C. R. (1987) J. Biol. Chem., 262, 15825–15828.
3 Marston, F. A. O. (1986) Biochem. J. 240, 1 12.
4 Macheroux, P., Massey, V., Thiele, D. J. and Volokita, M. (1991) Biochemistry 30, 4612–4619.
5 Studier, F. W., Rosenberg, A. H., Dunn, J. J. and Dubendorff, J. W. (1990) Methods Enzymol. 185, 60–89.
6 Sambrook, J., Fritsch, E. F. and Muniatis, T. (1989) Molecular Cloning: A Laboratory Manual, 2nd Edn., Cold Spring Harbor Laboratory, Cold Spring Harbor.
7 Arraj, J. A. and Marinum, M. G. (1983) J. Bacteriol. 153, 562–565
8 Bullock, W. D., Fernandez, J. M. and Georgiou, G. (1991) Biotechniques 5, 376.
9 Bowden, G. A., Parrdes, A. M. and Georgiou, G. (1992) Bio/Technology 9, 725–730
10 Zelitch, I. and Ochoa, S., (1953) J. Biol. Chem. 201, 707–718.
11 Frigerio, N. A. and Harbury, H. A. (1958) J. Biol. Chem. 231, 135–157
12 Kerr, M. W. and Groves, D. (1975) Phytochemistry 14, 359–362
13 Nishimura, M., Akhmedov, Y. D., Strazalka, K. and Akazawa, T. (1983) Arch. Biochem. Biophys. 222, 397–402.
14 Black, T. M., White, S. A., Reid, G. A. and Chapman, S. K. (1989) Biochem. J. 258, 255–259.
15 Lederer, F. (1991) in Chemistry and Biochemistry of Flavoenzymes (Müller, F., ed.), Vol. II, p. 153–242, CRC Press, Boca Raton
16 Cederlund, E., Lindqvist, Y. Söderlund, G., Branden, C.-I. and Jörnvall, H. (1988) Eur. J. Biochem. 173, 523–530
17 Hag, L. L., Juhn, D., Eggertson, G. and Söll, D (1991) J. Bacteriol. 173, 3408–3413
18 Balbas, P. and Bolivar, F. (1990) Methods Enzymol. 185, 14–37.

Having thus described and exemplified the invention with a certain degree of particularity, it should be appreciated that the following claims are not to be so limited but are to be afforded a scope commensurate with the wording of each element of the claim and equivalents thereof.

We claim:

1. In a process for preparing a mixture of glyoxylic acid and aminomethylphospohonic acid comprising the step of oxidizing glycolic acid with oxygen in an aqueous solution, the aqueous solution comprising aminomethylphospohonic acid and the enzymes glycolate oxidase and catalase, the improvement comprising:

(a) sparging oxygen into the aqueous solution; and (b) adding a catalyst to the mixture in the form of a microbial cell transformant that expresses glycolate oxidase, the microbial cell catalyst selected from the group consisting of transformants of *Aspergillus nidulans*, transformants of *Escherichia coli*, transformant *Pichia pastoris* GS115-MSP10 designated NRRL-Y-21001, and transformant *Hansenula polymorpha* G01 designated NRRL-Y-21065.

2. A process of claim 1 wherein said microbial cell catalyst also expresses endogenous catalase.

3. The process of claim 1 further comprising adding soluble catalase to the mixture.

4. The process of claim 1 wherein said microbial cell transformant is *Aspergillus nidulans* T17 designated NRRL-21000.

5. A process of claim 1 wherein said microbial cell catalyst is *Escherichia coli*.

* * * * *